(12) United States Patent
Upton et al.

(10) Patent No.: US 6,991,933 B1
(45) Date of Patent: Jan. 31, 2006

(54) CELL CULTURE SPINNER FLASKS

(75) Inventors: Todd M. Upton, Chestnut Hill, MA (US); John T. Flickinger, Beverly, MA (US)

(73) Assignee: Cytomatrix, LLC, Woburn, MA (US)

( * ) Notice: Subject to any disclaimer, the term of this patent is extended or adjusted under 35 U.S.C. 154(b) by 43 days.

(21) Appl. No.: 10/088,825

(22) PCT Filed: Sep. 22, 2000

(86) PCT No.: PCT/US00/26122

§ 371 (c)(1),
(2), (4) Date: Aug. 30, 2002

(87) PCT Pub. No.: WO01/21760

PCT Pub. Date: Mar. 29, 2001

Related U.S. Application Data

(63) Continuation-in-part of application No. 09/405,477, filed on Sep. 24, 1999, now abandoned.

(51) Int. Cl.
*C12M 3/00* (2006.01)

(52) U.S. Cl. .................... 435/299.2; 435/177; 435/395; 435/302.1

(58) Field of Classification Search ................. 435/395, 435/396, 397, 403, 243, 289.1, 295.3, 238.1, 435/297.2, 297.3, 299.1, 299.2, 302.1, 304.1, 435/304.2, 177–182; 210/616–619, 150
See application file for complete search history.

(56) References Cited

U.S. PATENT DOCUMENTS

| | | | |
|---|---|---|---|
| 3,622,129 A | 11/1971 | Mazowski et al. | 259/107 |
| 4,355,906 A | 10/1982 | Ono et al. | 366/274 |
| 4,683,062 A * | 7/1987 | Krovak et al. | 210/617 |
| 5,266,476 A | 11/1993 | Sussman et al. | 435/240.23 |
| 5,282,861 A | 2/1994 | Kaplan | 623/16 |
| 5,728,577 A * | 3/1998 | Kuriyama | 435/299.1 |
| 6,245,236 B1 * | 6/2001 | Schenck | 210/615 |

FOREIGN PATENT DOCUMENTS

| | | | |
|---|---|---|---|
| DE | 195 46 542 | | 5/1997 |
| EP | 0 421 211 | | 4/1991 |
| GB | 2 097 817 | | 11/1982 |
| JP | 02042974 A | * | 2/1990 |
| JP | 02280823 A | * | 11/1990 |
| JP | 04126068 | | 4/1992 |
| JP | 04126068 A | * | 4/1992 |
| WO | WO 99/15629 | | 1/1999 |

* cited by examiner

*Primary Examiner*—William H. Beisner
(74) *Attorney, Agent, or Firm*—Wolf, Greenfield & Sacks, PC

(57) ABSTRACT

The present invention relates to culturing devices that are compact, utilize small amounts of cell culture media to establish and maintain cell cultures, and produce a large number of cells in a short period of time when compared to other cell culturing devices and techniques. Such devices are useful in the culture of all cell types, but are particularly useful in the culture of cells that are known in the art to be difficult to culture, including cells that lose one or more of their particular attributes/characteristics (e.g., pluripotentiality), or cells that are difficult to establish cultures of (e.g., primary cells), during culture in traditional cell culture devices.

10 Claims, 7 Drawing Sheets

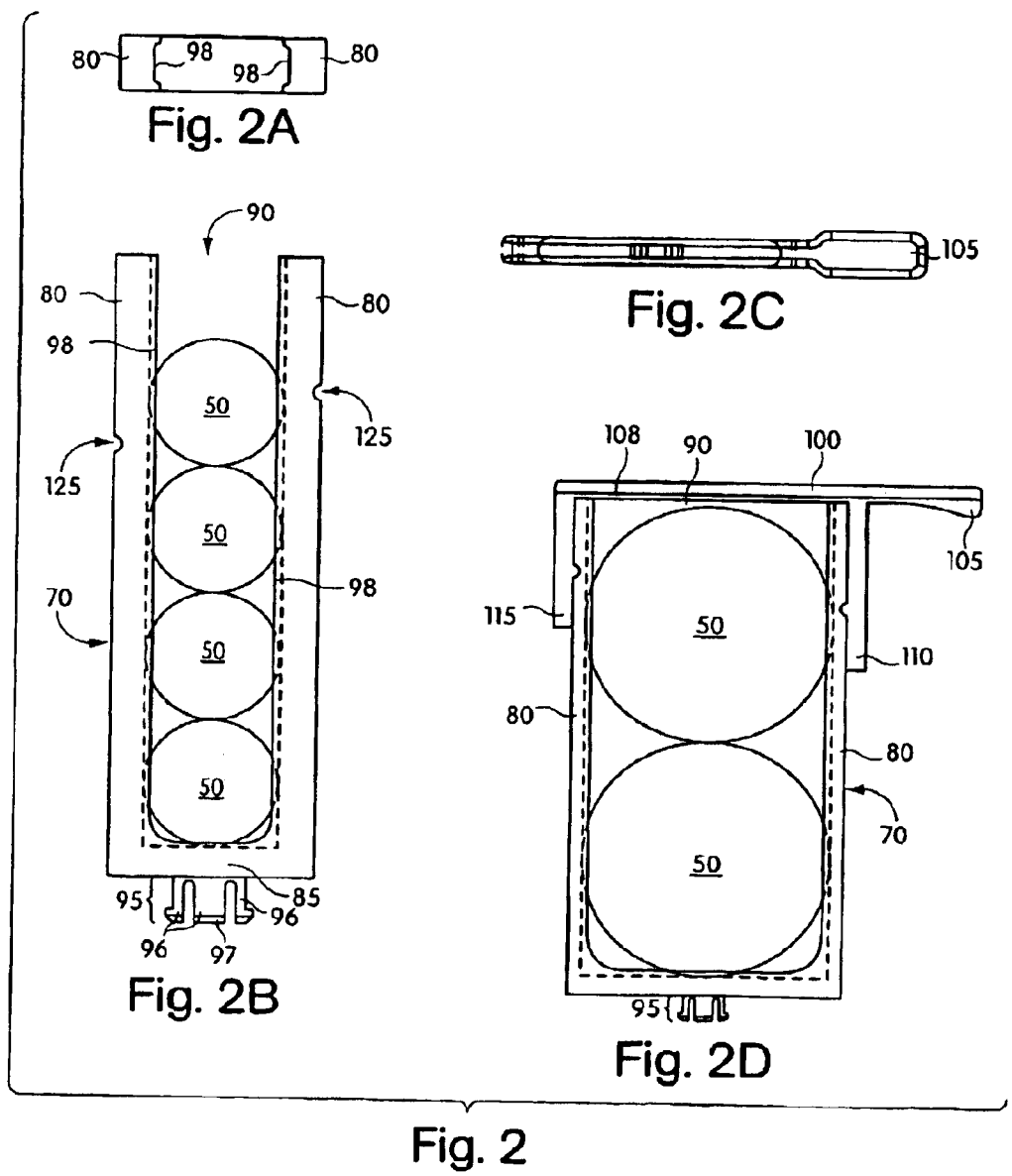

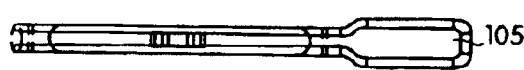
Fig. 3A
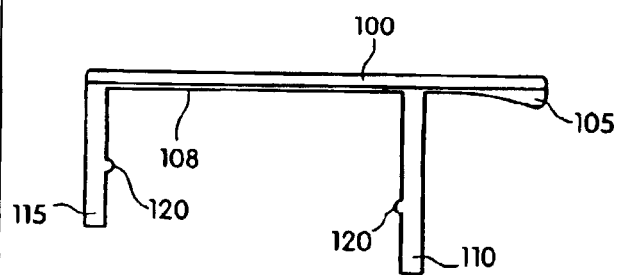
Fig. 3B
Fig. 3
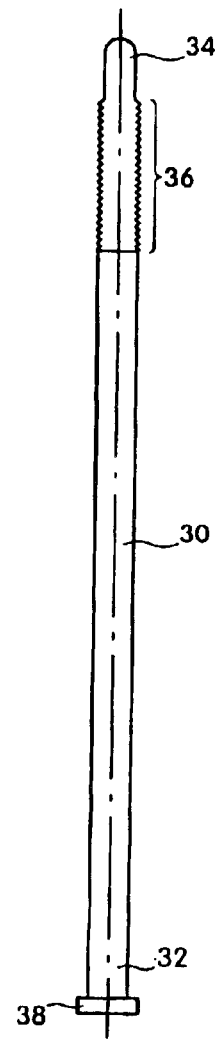
Fig. 4

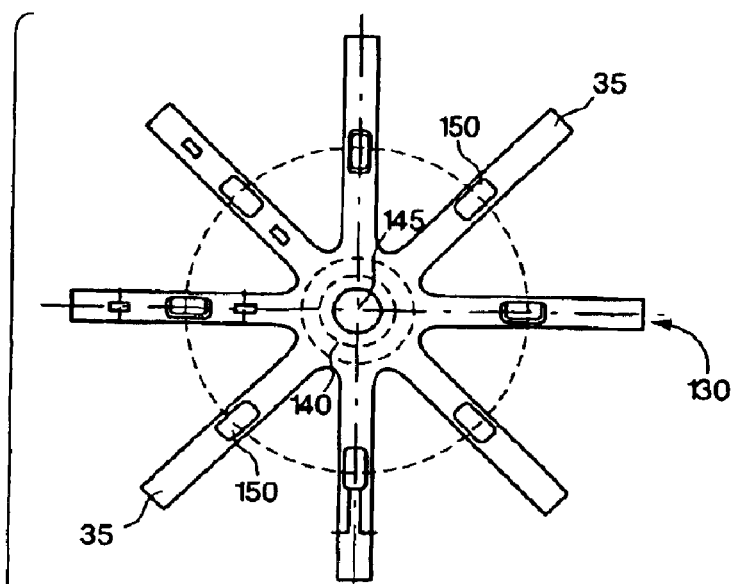
Fig. 5A
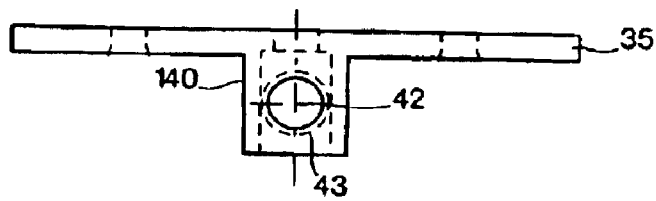
Fig. 5B
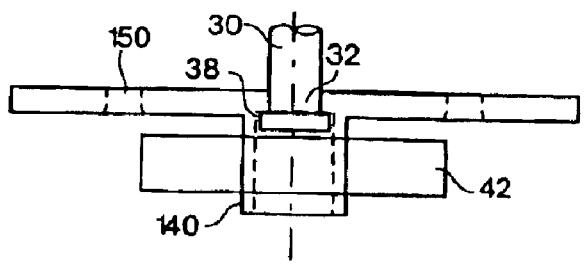
Fig. 5C
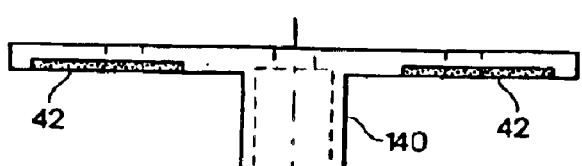
Fig. 5D
Fig. 5

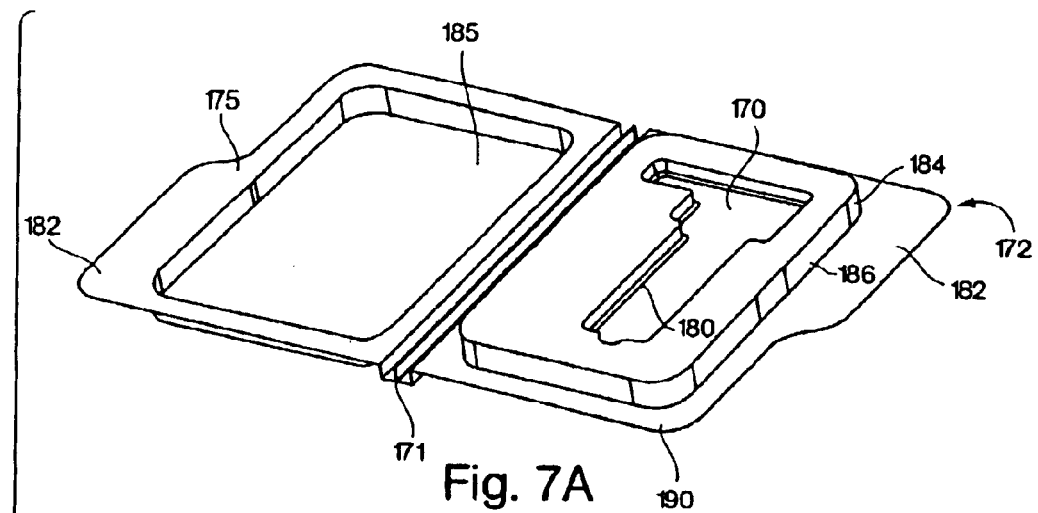
Fig. 7A
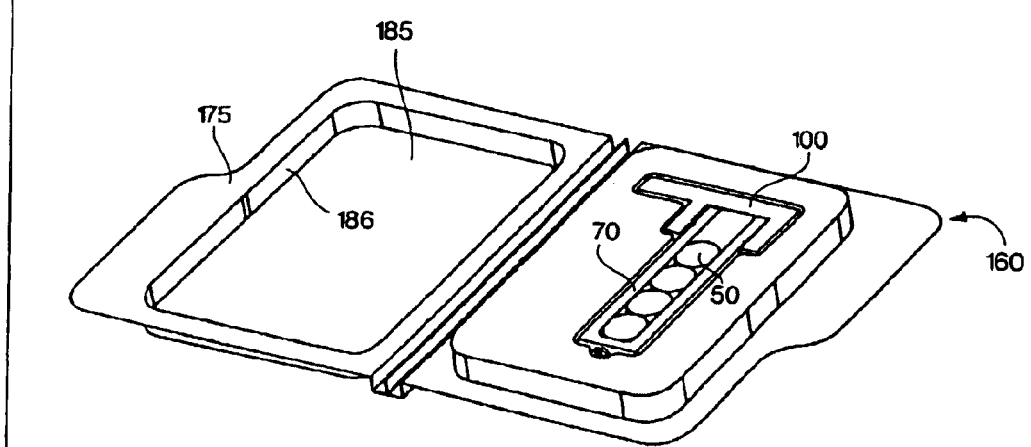
Fig. 7B
Fig. 7

CELL CULTURE SPINNER FLASKS

This application is a national stage filing under 35 U.S.C. § 371 of PCT International Application PCT/US00/26122, filed Sep. 22, 2000, which was published under PCT Article 21(2) in English, and is a continuation-in-part of U.S. application Ser. 09/405,477, filed Sep. 24, 1999, now abandoned.

FIELD OF THE INVENTION

In general the present invention relates to cell culturing, and in particular to improved methods and devices for culturing cells. In particular aspects, the invention relates to culturing cells in three-dimensional matrices.

BACKGROUND OF THE INVENTION

Cell culturing techniques and cell culturing devices are well known in the art.

U.S. Pat. No. 5,888,807, issued to Palsson, et al, on Mar. 30, 1999, describes bioreactors in which diverse cell types are simultaneously cultured in the presence of appropriate levels of nutrients and growth factors. Such levels are achieved by substantially continuously perfusing the cells in the bioreactor while removing undesirable metabolic products.

U.S. Pat. No. 5,712,154, issued to Mullon, et al., on Jan. 27, 1998, describes a cell culture system comprising liquid nutrient and gas perfusion fibers that provide the appropriate culture conditions for cells located interstitially between the liquid nutrient and gas fibers.

U.S. Pat. No. 5,320,963, issued Knaack, et al., on Jun. 14, 1994, describes a bioreactor for perfusion culture of cells in suspension. The bioreactor of Knaack et al. has an inversely-conical tank which includes a cell culture zone and a cell settling zone disposed annularly relative to the cell culture zone in the upper region of the tank.

SUMMARY OF THE INVENTION

The present invention provides culturing devices that are compact, utilize small amounts of cell culture media to establish and maintain cell cultures, and produce a large number of cells in a short period of time when compared to other cell culturing devices and techniques. Such devices are useful in the culture of all cell types, but are particularly useful in the culture of cells that are known in the art to be difficult to culture, including cells that lose one or more of their particular attributes/characteristics (e.g., pluripotentiality), or cells that are difficult to establish cultures of (e.g., primary cells), during culturing in traditional cell culture devices.

The invention, in one important part, involves improved methods and devices for culturing cells by providing cells an increased access to nutrients. We describe herein a cell culture system that takes advantage of biocompatible, open-pore, three-dimensional matrices, and uses movement of these matrices in culture media to increase accessibility of cells in culture on such matrices to media. Such culture system provides the appropriate conditions for the expansion and differentiation of most cell types.

According to one aspect of the invention, an apparatus for culturing cells is provided. The apparatus comprises a vessel for holding liquid cell culture media, a matrix assembly mounted in the vessel for movement in the media said matrix assembly including a support and a plurality of three-dimensional porous matrix members carried by the support for movement therewith, and a drive member operatively coupled to the support for moving it with the matrix members through the media. In one embodiment, the support includes a shaft, an outwardly extending member from and connected to the shaft, and a holder for carrying at least one three-dimensional porous matrix member and mounted on the outwardly extending member. In one embodiment, the holder is removably attached to the outwardly extending member. In certain embodiments, the outwardly extending member carries a plurality of holders. In further embodiments, at least one of the holders carries a plurality of three-dimensional porous matrix members. In a still further embodiment, the holder is permanently attached to the outwardly extending member.

In any of the foregoing embodiments, a plurality of outwardly extending members may extend radially outwardly from the shaft, each outwardly extending member carrying at least one holder. In important embodiments, the holder can be detachably connected to the outwardly extending member, and/or the holder can be mechanically coupled to the outwardly extending member for releasably retaining the holder on the outwardly extending member.

In any of the foregoing embodiments, the holder can be made of rigid plastic material and includes a U-shaped frame having an open and a closed end with a pair of opposed sides, said frame being attached at its closed end to the outwardly extending member, said sides having receptacles for receiving at least one three-dimensional porous matrix member and releasably holding the three-dimensional porous matrix member in place on the holder. In certain embodiments, the shaft can be supported in the vessel for rotation about the shaft axis. In important embodiments, the shaft can be supported vertically in the vessel and be supported therein from its top end. In further embodiments, the outwardly extending member can be disposed in the vicinity of the lower end of the shaft.

According to another aspect of the invention, an apparatus for culturing cells is provided. In this aspect of the invention the apparatus comprises a relatively rigid vessel for holding liquid cell culture media having an opening for providing access to its interior and a cover for the opening, a shaft disposed in the vessel and supported for rotation in the vessel by the cover, an outwardly extending member attached to the shaft extending outwardly from the axis of rotation of the shaft for rotation therewith, a plurality of holders attached to the outwardly extending member, and at least one three-dimensional porous matrix member carried by the holders for rotation with the shaft in the media.

In many embodiments, a motor drive is disposed outside the vessel and magnetically coupled to the shaft for rotating the shaft in media in the vessel. In a further embodiment, a motor drive is disposed outside the vessel and magnetically coupled to the member for rotating the holder in media in the vessel.

In any of the foregoing embodiments according to this aspect of the invention, the holder may comprise a pair of substantially parallel arms connected together at one end by a base arm and having an open end at the other, a mounting device connected to the base arm for mounting the holder to a support, and a groove in each of the arms generally facing one another to engage the at least one three-dimensional porous matrix member.

In any of the foregoing embodiments according to this aspect of the invention, a plurality of outwardly extending members may extend outwardly from the shaft, each of said members having at least one station for connection to the base arm of the holder. In certain embodiments, the station can comprise a recess, and the base arm of the holder may be connected to a mounting device (e.g., a peg) that fits into the recess to mechanically keep the holder in place on the outwardly extending member.

In any of the foregoing embodiments, the three-dimensional porous matrix member can have a circular and/or rectangular shape, and can have an edge that engages the arms.

According to another aspect of the invention, a matrix assembly for culturing cells is provided. The matrix assembly comprises a generally U-shaped holder having a pair of substantially parallel arms connected together at one end by a base arm and having an open end at the other, a mounting device joined to the base arm for mounting the holder to a support, a groove in each of the arms generally facing one another, and at least one three-dimensional porous matrix member having its periphery removably disposed between the groove of each arm. In some embodiments, a plurality of separate three-dimensional porous matrix members are mounted on the holder with their peripheries disposed in the grooves. The three-dimensional porous matrix member can have a circular and/or rectangular shape, or any other suitable shape complementary to the holder so as to enable the matrix to be removably mounted on the holder. In certain embodiments, the groove in each of the arms extends to the open end of the holder for enabling the periphery of the three-dimensional porous matrix member to be slipped into and between the grooves from the open end.

According to still another aspect of the invention, a matrix assembly is provided. The matrix assembly comprises a generally U-shaped holder having a pair of spaced apart coplanar arms connected together at one end by a base arm and having an open end at the other, at least one three-dimensional porous matrix member carried by the arms and detachably connected thereto, said three-dimensional porous matrix member being disposed between and in the plane of the arms, a mounting device attached to the base arm for mounting the holder to a support, and a closure-cap detachably mounted to the open end of the arms for preventing the three-dimensional porous matrix member being withdrawn from between the arms, said closure-cap having a handle for stripping the closure-cap from the holder and for carrying the assembly without touching the three-dimensional porous matrix member. In certain embodiments, the closure-cap has an end wall for spanning the open end space between the arms and a pair of legs for engaging the sides of the arms, and connectors on the arms and the legs for engaging one another to releasably hold the closure-cap in place on the holder. In important embodiments, the legs are of unequal length and the handle is disposed on the side of the closure-cap nearer the longer leg. In further important embodiments, the connectors are detents and recesses disposed on arms and the ends of the legs. In one embodiment, the connectors are disposed on the ends of the legs. In a further embodiment, the matrix assembly includes a plurality of three-dimensional porous matrix members disposed between the arms. Other types of connectors may be used as well, such as friction fits, snap fasteners, etc.

According to another aspect of the invention, a support-wheel for the holder in combination with the matrix assembly described in the preceding paragraph, is provided. The support-wheel comprises a hub, at least one arm extending outwardly from the hub, and at least one station on the at least one arm extending outwardly from the hub for receiving the mounting device of the holder as described elsewhere herein. In certain embodiments, the holder has a plurality of outwardly extending arms as described, and each arm carries at least one matrix assembly. In some embodiments, the at least one station on the arm of the support is an opening in the arm, and the mounting device of the holder is a snap fastener for engaging the opening.

According to yet another aspect of the invention, a support and matrix assembly for culturing cells is provided. The support and matrix assembly comprise a shaft for disposition in a vessel containing liquid cell culture media, a support-wheel mounted on the shaft and having a plurality of arms extending outwardly away from the shaft, each of said arms having at least one station for carrying a matrix assembly, a plurality of matrix assemblies mounted on each of the stations, each assembly including a U-shaped holder having a pair of generally parallel and spaced apart arms connected together at one end by a base arm and having an open end at the other, a mounting device attached to the base arm for mounting the holder to the station on the arm of the support-wheel, a groove on each of the arms of the holder facing one another for supporting three-dimensional porous matrix members between and generally in the plane of the arms, and a closure-cap for each of the holders for retaining the three-dimensional porous matrix member, between the arms. In certain embodiments, the support-wheel has eight arms. In preferred embodiments, each arm of the support-wheel has three stations. In important embodiments, each holder carries a plurality of three-dimensional porous matrix members. In further important embodiments, each holder can carry at least four three-dimensional porous matrix members.

In any of the foregoing embodiments, the holder and/or support can be made of plastic, and/or they can be disposable.

According to another aspect of the invention, a matrix cartridge for culturing cells is provided. The matrix cartridge comprises a generally U-shaped holder having a pair of spaced apart coplanar arms connected together at one end by a base arm and having an open end at the other, at least one three-dimensional porous matrix member carried by the arms and detachably connected thereto, said three-dimensional porous matrix member being disposed between and in the plane of the arms, a mounting device attached to the base arm for mounting the holder to a support, a closure-cap detachably mounted to the open end of the arms for preventing the three-dimensional porous matrix member being withdrawn from between the arms, said closure-cap having a handle for stripping the closure-cap from the holder and for carrying the assembly without touching the three-dimensional porous matrix member, and a container having a well for an assembled holder, closure-cap and three-dimensional porous matrix member, said container having a cover for sealing the well with the holder, closure-cap and three-dimensional porous matrix member. In important embodiments, the well shape conforms to the shape of the assembled holder, closure-cap and three-dimensional porous matrix member. In certain embodiments, the well supports the assembled holder, closure-cap and three-dimensional porous matrix member so that the matrix member does not physically engage the well or cover. In some embodiments, the well has a shoulder in the periphery that supports the holder away from the well bottom so that the three-dimensional porous matrix member does not engage said bottom.

According to another aspect of the invention, an apparatus for culturing cells is provided. The apparatus includes a vessel for holding liquid cell culture media, a matrix assembly mounted in the vessel for movement in the media, said matrix assembly including a support and at least one three-dimensional porous matrix member carried by the support for movement therewith, and drive means operatively coupled to the support for moving it with the matrix members through the media. In certain embodiments, the support includes a shaft means, means extending away form the shaft means, and means for carrying at least one three-dimensional porous matrix member and mounted on the means extending away form the shaft means. In some embodiments, drive means can be magnets, motors, cams, and pulleys.

According to still another aspect of the invention, an apparatus for culturing cells is provided. The apparatus includes a relatively rigid vessel for holding liquid cell culture media having an opening for providing access to its interior and a cover for the opening, first means disposed in the vessel and supported in the vessel by the cover, an outwardly extending member attached to the first means and rotatable in the vessel, a plurality of holders attached to the outwardly extending member, and three-dimensional porous matrix members carried by the holders, and means for moving the outwardly extending member with the holders in the media.

According to a further aspect of the invention, a matrix assembly, is provided. The matrix assembly includes a holder having means for mounting the holder to a support, engaging means on the holder for carrying a three-dimensional porous matrix member, and at least one three-dimensional porous matrix member attached to the holder by the engaging means.

According to a further aspect of the invention, a support and matrix assembly for culturing cells, is provided. The support and matrix assembly comprise support means for disposition in a vessel containing liquid cell culture media, at lease one matrix assembly mounted on the support means and carrying at least one three-dimensional porous matrix member, and a closure-cap operatively associated with the holder for retaining the matrix member on the holder. In certain embodiments, the matrix assembly includes a holder having a pair of arms for engaging the matrix member, and wherein the closure-cap has a leg that releasably engages the arms.

According to still another aspect of the invention, a matrix cartridge for culturing cells is provided. The a matrix cartridge comprises a holder having a means for detachably supporting at least one three-dimensional porous matrix member, a closure-cap mounted to the holder for preventing the matrix member from being withdrawn from the holder, said closure-cap having gripping means for removing the cap from the holder and for carrying the holder without touching the matrix member, and a sealable closure for the holder, closure-cap and matrix member when they are assembled together.

According to another aspect of the invention, a method for in vitro culture of cells, is provided. The method involves introducing an amount of cells into a three-dimensional porous matrix having interconnected pores of a pore size sufficient to permit the cells to grow throughout the matrix, culturing the cells under conditions sufficient to allow the cells to adhere to the three-dimensional porous matrix, and moving the three-dimensional porous matrix in a liquid cell culture medium under conditions sufficient to promote maintenance, expansion, or differentiation of the cells. In certain embodiments, the cells are selected from the group consisting of mammalian cells, animal cells, plant cells, eukaryotic cells, prokaryotic cells and genetically engineered cells. In important embodiments, the cells are hematopoietic progenitor cells.

In some embodiments, the hematopoietic progenitor cells are cultured under conditions and for a time sufficient to increase the number of hematopoietic progenitor cells relative to the amount introduced the three-dimensional porous matrix. In certain embodiments, the conditions may exclude exogenously added agents. An exogenously added agent is an agent selected from the group consisting of a hematopoietic growth factor that promotes hematopoietic cell maintenance, expansion and/or differentiation, inoculated stromal cells, and stromal cell conditioned medium.

In further embodiments, the foregoing in vitro hematopoietic progenitor cell culture methods may further comprise before the introducing step, obtaining the hematopoietic progenitor cells from a blood product. The blood product can be unfractionated bone marrow.

The culture methods, in certain embodiments, may further comprise harvesting cells. The harvesting may comprise a first harvesting after a first culturing period, and at least one additional harvesting after at least one additional culturing period.

Any of the foregoing in vitro cell culture methods of the invention are preferably performed using any of the foregoing numerous devices of the invention.

In any of the foregoing embodiments, the three-dimensional porous matrix (member) comprises a porous matrix that can be one that is an open cell porous matrix having a percent open space of at least 50%, and preferably at least 75%. In one embodiment the porous matrix has pores defined by interconnecting ligaments having a diameter at midpoint on average, of less than 150 $\mu$n. Preferably the porous matrix is a metal-coated reticulated open cell foam of carbon containing material, the metal coating being selected from the group consisting of tantalum, titanium, platinum (including other metals of the platinum group), niobium, hafnium, tungsten, and combinations thereof. In preferred embodiments, whether the porous matrix is metal-coated or not, the matrix is coated with a biological agent selected from the group consisting of collagens, fibronectins, laminins, integrins, angiogenic factors, anti-inflammatory factors, glycosaminoglycans, vitrogen, antibodies and fragments thereof, functional equivalents of these factors (including fragments thereof), and combinations thereof. Most preferably the metal coating is tantalum coated with a biological agent. In preferred embodiments of the invention the porous matrices are solid, unitary macrostructures, i.e. not beads or packed beads. They also involve nonbiodegradable materials.

These and other objects of the invention will be described in further detail in connection with the detailed description of the invention.

BRIEF DESCRIPTION OF THE DRAWINGS

FIG. 2 is a schematic showing different views of two alternative types of holders used in the invention; FIG. 2A is a bottom cross-sectional view of the holder depicted in the side cross-sectional view of FIG. 2B; FIG. 2C is a bottom cross-sectional view of the holder depicted in a side cross-sectional view in FIG. 2D.

FIG. 3 is a schematic showing a top cross-sectional view (FIG. 3A), and a side cross-sectional view (FIG. 3B) of a closure-cap of the invention.

FIG. 4 is a schematic cross-sectional view of a shaft used in one of the apparatuses of the invention.

FIG. 5 is a schematic showing different views of alternative types of a support-wheel used in an apparatus of the invention; FIG. 5A shows a top cross-sectional view of a support-wheel; FIG. 5B shows a side cross-sectional view of the support-wheel depicted in FIG. 5A; FIG. 5C shows a side cross-sectional view of the support-wheel depicted in FIG. 5B turned at a 90° angle; and FIG. 5D shows a side cross-sectional view of a support-wheel according to a different embodiment.

FIG. 7 is a perspective view of a matrix cartridge of the invention; FIG. 7A depicts a container (empty matrix cartridge), and FIG. 7B depicts a matrix cartridge in the open configuration that contains an assembled holder, closure-cap and three-dimensional porous matrix members.

DETAILED DESCRIPTION OF THE INVENTION

Figure 1:
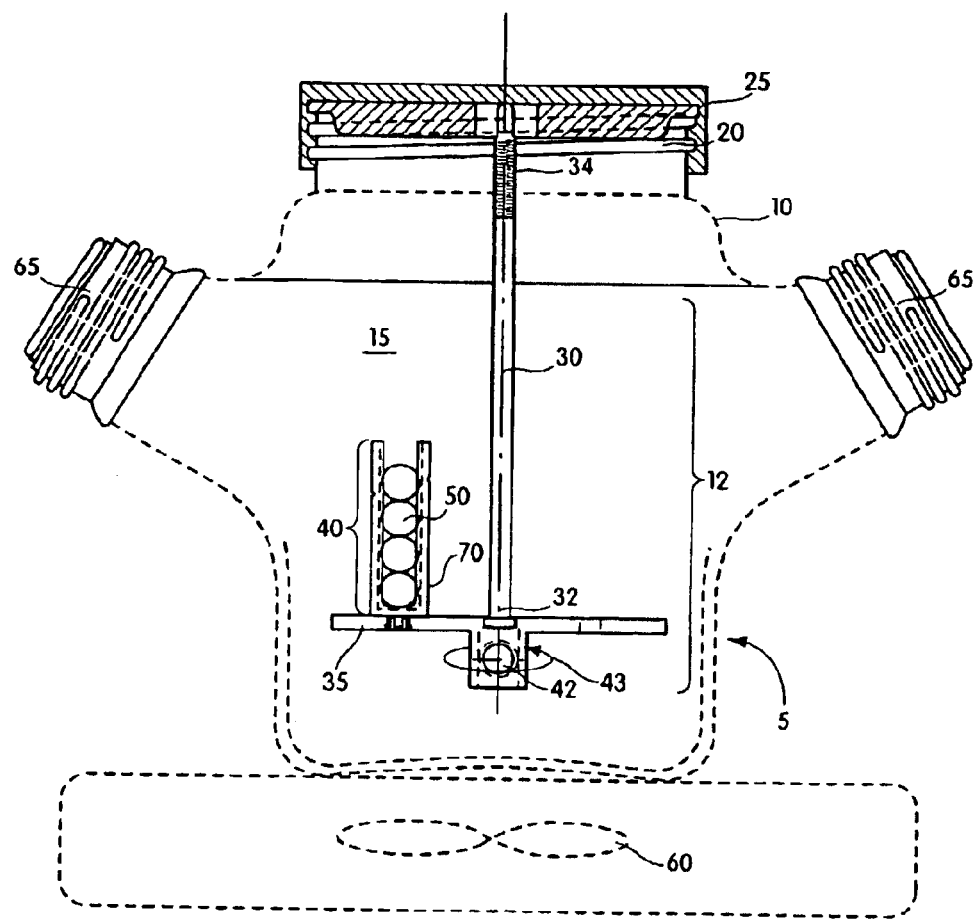
FIG. 1 is a schematic cross-sectional side view of an apparatus of the invention.

The invention provides various apparatus for carrying out the methods of the invention. A preferred apparatus is depicted in FIG. 1. The principle components of the embodiment depicted in FIG. 1 are apparatus 5 which comprises a relatively rigid vessel 10 for holding liquid cell culture media 15. Vessel 10 may be made from plastic, teflon material, polycarbonate, polystyrene, glass, silicone, rubber, polypropylene, stainless steel, nylon, polyester or any combinations thereof, or any other similar material. A preferred material to be used for the manufacture of such vessel 10, according to the invention is polystyrene. In one embodiment the shape of the rigid vessel 10, as depicted in FIG. 1, is generally cylindrical, but the shape of vessel 10 may vary widely. For example, the vessel may be rectangular, elliptical, or any other shape that enables the mechanical assembly within it to rotate or otherwise move in the media also in the vessel.

Apparatus 5 further comprises a matrix assembly 40 mounted in the vessel 10 for movement in the media 15. The matrix assembly as depicted in FIG. 1, includes a support 12 and a plurality of three-dimensional porous matrix members 50 carried by the support 12 for movement therewith. As depicted in FIG. 1 the support 12 comprises a shaft 30 disposed in the vessel 10 and supported for rotation in the vessel by a vessel cover 25. Support 12 further comprises an outwardly extending member 35 attached to shaft 30 and extending outwardly from the axis of rotation of the shaft for rotation in the media. Support 12 further comprises a generally U-shape holder 70 attached to the outwardly extending member 35 for carrying at least one three-dimensional porous matrix member 50 for rotation with the shaft 30 in the media 15. While in the embodiment illustrated the holder 70 attached to the outwardly extending member 35 appears in the upright position, holder 70 may be attached to the outwardly extending member 35 so that it appears suspended from the member 35.

Apparatus 5 further comprises a drive member 42 which is operatively coupled to the support 12 by being accommodated in opening 43 of support 12, for moving with the matrix assembly 40 through the media. The drive member 42 can be, for example, a stirrer assembly (magnet). The stirrer assembly can be magnetically coupled to a motor drive 60 (e.g., magnetic motor drive) disposed outside the vessel 10, thus allowing the shaft 30 and its attached outwardly extending members 50 and matrix assembly 40 mounted thereon, to rotate in the media 15 in the vessel 10. Drive member 42 can also be a motor, cam, pulley, and the like.

The shaft 30 as depicted in the apparatus 5 in FIG. 1 is supported vertically in the vessel 10 from its top end 34. Shaft 30 can be permanently attached to cover 25 or it can be releasably attached to cover 25. Shaft 30 can be made from materials similar to the materials used in the manufacture of rigid vessel 10, preferably polystyrene. While in the embodiment illustrated the shaft 30 is supported from the top by the cover 25, the shaft may be supported independently of the cover above and/or below the member 35 for example by a web or spider-like member that is seated on the bottom of the vessel or attached to the vessel sides or rim below the cover. In a preferred embodiment of the invention the shaft 30 is securely attached to the vessel (e.g., from the vessel's cover), does not itself rotate, but provides support for a matrix assembly and support means, for example, an outwardly extending member 35 and/or a support-wheel 130, said support means allowed to freely rotate upon the shaft.

Vessel 10 may be provided with one or more openings 65 which may be used for a number of purposes. For example, one or more of opening 65 may be used to allow a measuring device or measuring devices to be inserted into the vessel 10 through the opening(s) 65 and into the culture media 15 contained in vessel 10 to measure conditions therein. Opening(s) 65 may also be used as fluid inlet and fluid outlet ports which would permit adding and removing culture media 15 to and from the vessel 10 on a continuous basis or on a per batch basis.

Turning now to the drawings of FIG. 2 of the invention, FIG. 2 include schematics that depict different views (bottom and side cross-sectional views) of two different types of holder assemblies. FIG. 2B is a side cross-sectional view of a holder 70. Holder 70 comprises a pair of substantially parallel arms 80 connected together at one end by a base arm 85 and having an open end 90 at the other. A mounting device 95 is connected to the base arm 85 of holder 70 for mounting holder 70 to a support. The station mounting device 95 in the illustrated embodiment is in the form of a snap fastener having flexible teeth 96 with flanges 97 at the bottom that fit into, for example, the opening of station to retain the holder in place. Other types of connectors of covers may be used such as bayonet-type connectors, threads, friction fit, etc., that will enable the holder to be readily mounted in place. Holder 70 further comprises a groove 98 in each of the arms generally facing one another. Groove 98 is useful in releasably engaging at least one three-dimensional porous matrix member 50. Four such three-dimensional porous matrix members are depicted in FIG. 2B. While the holder 70 in the embodiment illustrated has a pair of parallel arms with grooves 98 to engage the edges of the matrix members 50, other configurations may be employed. For example, two closely spaced arms on each side of the holder may together engage the members in the space between them. Moreover, the arms need not be parallel so long as they have seats to receive the edges spaced apart the appropriate distance to accommodate the matrix members.

FIG. 2A is a bottom cross-sectional view of the holder 70 depicted in FIG. 2B. Groove 98 on each of the arms 80 of holder 70 can be clearly shown.

FIG. 2D is a side cross-sectional view of a holder 70 according to another embodiment of the invention. In this particular configuration, only two larger size three-dimensional porous matrix members 50 are carried by the holder 70. In addition to holder 70. FIG. 2D also depicts a closure-cap 100 which is detachably mounted to the open end 90 of holder 70 for preventing the three-dimensional porous matrix members 50 being withdrawn from between the arms. The closure-cap 100 preferably includes a handle 105 for stripping the closure-cap 100 from the holder 70, and for carrying the holder assembly (holder 70 and three-dimensional porous matrix members 50), without touching the three-dimensional porous matrix members 50.

FIG. 2C is a top cross-sectional view of the holder 70 described above in FIG. 2D.

The views of FIG. 3 are schematic representation of a closure-cap 100 assembly. FIG. 3B is a cross-sectional side view of a closure-cap 100. Closure-cap 100 has an end wall 108 for spanning the open end space 90 between the arms 80 of holder 70, and comprises a pair of legs (110 and 115) for engaging the sides of the arms 80 of holder 70. Legs 110 and 115 are of unequal length, and the handle 105 is disposed on the side of the closure-cap nearer the longer leg 110. Also depicted in FIG. 3B are connectors 120 in the form of detents on the surface of each leg that comes into contact with holder 70. Such connectors are useful in combination with equivalent connectors (e.g., recesses 125-FIG. 2B) on the outside edges of arms 80 of holder 70, to engage one another so that the closure-cap 100 can be releasably held in place on the holder 70. While the connectors on the legs 110 and 115 of the cap and 125 on the arms of the holder 70 are shown as bumps and recesses to releasably hold the cap in place, the connectors may take other shapes such as, for example, undercuts and steps on the arms and legs to hold the caps in place, or the legs and arms may simply frictionally engage one another.

FIG. 3A is a top cross-sectional view of the closure-cap 100 of the invention. Handle 105 is of slightly larger width than the portion of the closure-cap that engages the holder 70 that allows for easier handling. The configuration of the handle 105 and legs 110 and 115 allows the cap to be removed most conveniently by simply pressing down on the handle 105 so as to cause the cap to pivot about the top of the arms of the holder nearer to the handle or about the lower end of the leg 110, causing the shorter leg 115 and its connector 120 to release the arm of the holder that it normally engages. In another embodiment, the handle may be mounted on the side of the shorter leg 115 in which case the cap may be removed by pulling up on the handle 105.

FIG. 4 is a cross-sectional side view of a shaft 30 according to one embodiment of the invention. Shaft 30 has a top end 34 and a lower end 32. Proximal to the top end 34 of shaft 30 is a threaded portion 36 that allows shaft 30 to be releasably attached to a cover 25 of a rigid vessel 10 (e.g., by screwing). Distally to lower end 32 of shaft 30 is the end portion 38 of shaft 30. End portion 38 has a larger diameter than the diameter of shaft 30. This increased diameter allows, for example, for the support of a support-wheel 130 (as depicted below in the views of FIG. 5) to be releasably attached to shaft 30, and to freely rotate independent of shaft 30. While in the embodiment illustrated the shaft is threadedly connected to the cover 25 (and preferably remains stationary), it should be understood that in different embodiments the shaft may be rotatably mounted with respect to the cover by bearings so that the shaft may rotate with the support wheel 130 and/or relative to the cover 25 as described more fully below. In a further embodiment, the shaft may be permanently attached to vessel 10 (to cover 25 or to some other vessel part, therefore acting as an axle), the support-wheel may be permanently attached to the shaft 30 (or to some other vessel part), the matrix assembly 40 may be permanently attached to the support-wheel 130, wherein vessel 10 is preferably cylindrical, and vessel 10 may itself be rotated so that matrix members can move with respect to media contained therein.

The holder 70 of the invention can be permanently attached or detachably attached to a support (e.g., outwardly extending arm 35 of a support wheel 130—see FIG. 5).

FIG. 5 is a schematic representation of a top cross-sectional view (FIG. 5A) and a side cross-sectional view (FIG. 5B) of a support-wheel 130 according to one embodiment of the invention. The support-wheel 130 as depicted in FIG. 5, comprises a hub 140, at least one arm 35 extending outwardly from the hub 140, and at least one station 150 on the arm 35 extending outwardly from the hub 140 for receiving the mounting device 95 of a holder 70. In one embodiment, the support-wheel 130 depicted in FIG. 5A has a hole 145 in the middle of hub 140. Such hole 145 on the support-wheel allows the support-wheel to be sled onto the shaft 30 and supported therewith from shaft end 38 (see FIG. 4). FIG. 5B depicts a cross-sectional side view of a support-wheel 130. A drive member 42 (e.g., a stirrer assembly) can be accommodated in hole 43 of support-wheel 130. FIG. 5C depicts a cross-sectional side view of the support-wheel 130 as shown in FIG. 5B turned at a 90° angle. FIG. 5D depicts a cross-sectional side view of a support-wheel 130 according to a different embodiment of the invention where drive members 42 (e.g., magnets) are integrated (i.e. built-in or attached) into at least one of the outwardly extending members 35 of the support-wheel 130. A support-wheel in a different embodiment may be simply a platform of circular or any other shape.

The station 150 in the illustrated embodiment is a non-circular opening in the arm 35 of the support-wheel that receives the mounting device 95 in the form of a snap fastener having flexible teeth 96 with flanges 97 at the bottom that fit into the opening to retain the holder in place. The non-circular configuration is a convenient expedient to use if a specific orientation of the holder on the arm is desired and it is not supposed to be limiting in any way as to the shape of the station. Other types of connectors of covers may be used such as bayonet-type connectors, threads, friction fit, etc., that will enable the holder to be readily mounted in place.

Figure 6:
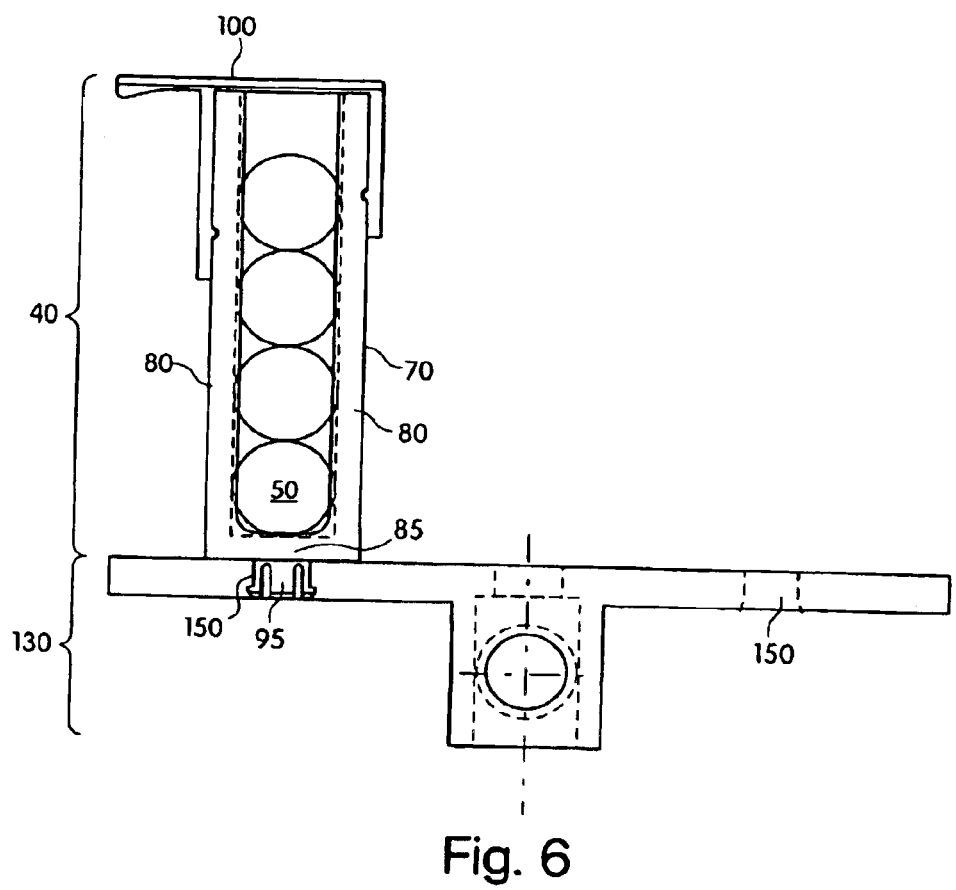
FIG. 6 is a schematic side cross-sectional view of a matrix assembly of the invention in relation to a support.

FIG. 6 is a schematic cross-sectional side view of a matrix assembly 40 in relation to a support-wheel 130. In this particular aspect of the invention, matrix assembly 40 comprises a holder 70 which supports four three-dimensional porous matrix members 50, and a closure-cap on the holder for retaining the three-dimensional porous matrix members 50 between the arms 80 of the holder 70. A mounting device 95 is shown attached to the base arm 85 of the holder 70 for mounting the holder to a support (e.g., a support-wheel 130).

FIG. 7 is a perspective view of a matrix cartridge for culturing cells of the invention. A matrix cartridge is useful for inoculating and culturing (at first) cells according to the invention. Both FIGS. 7A and 7B depict a matrix cartridge in an open configuration.

FIG. 7A depicts a container 172 (e.g., an empty matrix cartridge). The container 172 comprises a well 170 for an assembled holder 70, closure-cap 100 and three-dimensional porous matrix members 50. The container also has a cover 175 for sealing the well 170 with the holder 70, closure-cap 100 and three-dimensional porous matrix members 50. Both the empty matrix cartridge 172 depicted in 7A, and loaded matrix cartridge 160 as depicted in FIG. 7B, have wells 170 whose shape conforms to the shape of the assembled holder 70, closure-cap 100 and three-dimensional porous matrix member 50. According to one embodiment of the invention, the container 172 depicted in FIG. 7A, comprises a well 170 having a shoulder 180 in the periphery that supports the holder 70 away from the well bottom, so that the three-dimensional porous matrix member(s) does not engage the bottom of the well 170. The container 172 may typically be made of plastic material such as polystyrene, and may be vacuum formed or molded with a live hinge 171 forming the base 190 and cover 175. The margins 182 about the base and cover may be sealed together so as to, for example, maintain a sterile atmosphere for the holder, cap and matrix members, and/or prevent excessive evaporation of media during culturing of cells in situ (e.g., for the first culturing step: inoculation of matrix with cells and incubation for cell adherence). In the embodiment shown, undercuts 186 are provided on the sides 184 of the base 172 and the recess 185 in the cover 175 to hold the container closed. Other forms of seals may be used. For example, the margins 182 of the base 190 and cover 175 may be ultrasonically or adhesively joined together.

In an important aspect, the invention embraces methods for in vitro culture of cells. A method according to this aspect of the invention involves introducing an amount of cells into a three-dimensional porous matrix having interconnected pores of a pore size sufficient to permit the cells to grow throughout the matrix, culturing the cells under conditions sufficient to allow the cells to adhere to the three-dimensional porous matrix, and moving the three-dimensional porous matrix in a liquid cell culture medium under conditions sufficient to promote maintenance, expansion, or differentiation of the cells.

"Conditions sufficient to allow the cells to adhere" to the three-dimensional porous matrix or any other tissue culture substrate, are conditions well known in the art. Such conditions simply involve allowing sufficient time for the cells to adhere to the substrate, and such conditions will vary with the type of cells in culture, the type of substrate (e.g., plastic, metal, coated plastic, coated metal, etc.), culture environment such as temperature, media, $CO_2/O_2$ levels, etc. One of ordinary skill in the art could easily determine such conditions. Typically, cells can adhere to a substrate in as little as 5 minutes. Preferably, cells of the invention cultured in any of the devices of the invention are left to adhere to a substrate, such as Cellfoam, for as little as 0.5 hour and 24 hours maximum, before proceeding with the remaining steps of the cell culture methods of the invention.

In some embodiments, the cells are selected from the group consisting of mammalian cells, animal cells, plant cells, eukaryotic cells, prokaryotic cells and genetically engineered cells. In certain embodiments, the cells are hematopoietic progenitor cells.

In some embodiments, the hematopoietic progenitor cells are cultured under conditions and for a time sufficient to increase the number of hematopoietic progenitor cells relative to the amount introduced the three-dimensional porous matrix. In certain embodiments, the conditions may exclude exogenously added agents. An exogenously added agent is an agent selected from the group consisting of a hematopoietic growth factor that promotes hematopoietic cell maintenance, expansion and/or differentiation, inoculated stromal cells, and stromal cell conditioned medium.

Preferably, the cells being cultured on the three-dimensional matrix members used in various embodiments of the invention are animal cells, plant cells, eukaryotic cells, prokaryotic cells, mammalian cells, or genetically engineered cells. The cells being grown may be from one or more cell lines, and the cells being grown may be tissues or components of tissues. Also, the cells being grown may be multi-cell assemblies.

In an important embodiment of the invention, the cultured cells are hematopoietic progenitor cells. "Hematopoietic progenitor cells," as used herein, refer to immature blood cells having the capacity to self-renew and to differentiate into the more mature blood cells (also described herein as "progeny") comprising granulocytes (e.g., promyelocytes, neutrophils, eosinophils, basophils), erythrocytes (e.g., reticulocytes, erythrocytes), thrombocytes (e.g., megakaryoblasts, platelet producing megakaryocytes, platelets), and monocytes (e.g. monocytes, macrophages). It is known in the art that such cells may or may not include $CD34^+$ cells. $CD34^+$ cells are immature cells present in the "blood products" described below, express the CD34 cell surface marker, and are believed to include a subpopulation of cells with the "progenitor cell" properties defined above. It is well known in the art that hematopoietic progenitor cells include pluripotent stem cells, multipotent progenitor cells (e.g., a lymphoid stem cell), and/or progenitor cells committed to specific hematopoietic lineages. The progenitor cells committed to specific hematopoietic lineages may be of T cell lineage, B cell lineage, dendritic cell lineage, Langerhans cell lineage and/or lymphoid tissue-specific macrophage cell lineage.

The hematopoietic progenitor cells can be obtained from blood products. A "blood product" as used in the present invention defines a product obtained from the body or an organ of the body containing cells of hematopoietic origin. Such sources include unfractionated bone marrow, umbilical cord, peripheral blood, liver, thymus, lymph and spleen. It will be apparent to those of ordinary skill in the art that all of the aforementioned crude or unfractionated blood products can be enriched for cells having "hematopoietic progenitor cell" characteristics in a number of ways. For example, the blood product can be depleted from the more differentiated progeny. The more mature, differentiated cells can be selected against, via cell surface molecules they express. Additionally, the blood product can be fractionated selecting for $CD34^+$ cells. As mentioned earlier, $CD34^+$ cells are thought in the art to include a subpopulation of cells capable of self-renewal and pluripotentiality. Such selection can be accomplished using, for example, commercially available magnetic anti-CD34 beads (Dynal, Lake Success, N.Y.). Unfractionated blood products can be obtained directly from a donor or retrieved from cryopreservative storage.

The hematopoietic progenitor cells can be co-cultured with other cell types, including lymphoreticular stromal cells. "Lymphoreticular stromal cells" as used herein may include, but are not limited to, all cell types present in a lymphoid tissue which are not lymphocytes or lymphocyte precursors or progenitors, e.g., epithelial cells, endothelial cells, mesothelial cells, dendritic cells, splenocytes and macrophages. Lymphoreticular stromal cells also include cells that would not ordinarily function as lymphoreticular stromal cells, such as fibroblasts, which have been genetically altered to secrete or express on their cell surface the factors necessary for the maintenance, growth and/or differentiation of hematopoietic progenitor cells, including their progeny. Lymphoreticular stromal cells are derived from the disaggregation of a piece of lymphoid tissue (see discussion below and the Examples). Such cells according to the invention are capable of supporting in vitro the maintenance, growth and/or differentiation of hematopoietic progenitor cells, including their progeny. By "lymphoid tissue" it is meant to include bone marrow, peripheral blood (including mobilized peripheral blood), umbilical cord blood, placental blood, fetal liver, embryonic cells (including embryonic stem cells), aortal-gonadal-mesonephros derived cells, and lymphoid soft tissue. "Lymphoid soft tissue" as used herein includes, but is not limited to, tissues such as thymus, spleen, liver, lymph node, skin, tonsil, adenoids and Peyer's patch, and combinations thereof.

Lymphoreticular stromal cells provide the supporting microenvironment in the intact lymphoid tissue for the maintenance, growth and/or differentiation of hematopoietic progenitor cells, including their progeny. The microenvironment includes soluble and cell surface factors expressed by the various cell types which comprise the lymphoreticular stroma. Generally, the support which the lymphoreticular stromal cells provide may be characterized as both contact-dependent and non-contact-dependent.

Lymphoreticular stromal cells may be autologous ("self") or non-autologous ("nonself," e.g., allogeneic, syngeneic or xenogeneic) with respect to hematopoietic progenitor cells or antigen presenting cells. "Autologous," as used herein, refers to cells from the same subject. "Allogeneic," as used herein, refers to cells of the same species that differ genetically to the cell in comparison. "Syngeneic," as used herein, refers to cells of a different subject that are genetically identical to the cell in comparison. "Xenogeneic." as used herein, refers to cells of a different species to the cell in comparison. Lymphoreticular stroma cells may be obtained from the lymphoid tissue of a human or a non-human subject at any time after the organ/tissue has developed to a stage (i.e., the maturation stage) at which it can support the maintenance growth and/or differentiation of hematopoietic progenitor cells. The stage will vary between organs/tissues and between subjects. In primates, for example, the maturation stage of thymic development is achieved during the second trimester. At this stage of development the thymus can produce peptide hormones such as thymulin, $\alpha_1$ and $\beta_4$-thymosin, and thymopoietin, as well as other factors required to provide the proper microenvironment for T cell differentiation. The different maturation stages for the different organs/tissues and between different subjects are well known in the art.

The lymphoid tissue from which lymphoreticular stromal cells are derived usually determines the lineage-commitment hematopoietic progenitor cells undertake, resulting in the lineage-specificity of the differentiated progeny. In certain embodiments, the lymphoreticular stromal cells are thymic stromal cells and the multipotent progenitor cells and/or committed progenitor cells are committed to a T cell lineage. In other embodiments, the lymphoreticular stromal cells may be splenic stromal cells and the multipotent progenitor cells and/or committed progenitor cells are committed to a B cell lineage.

Employing the culture conditions described in greater detail below, it is possible according to the invention to preserve hematopoietic progenitor cells and to stimulate the expansion of hematopoietic progenitor cell number and/or colony forming unit potential. Once expanded, the cells, for example, can be returned to the body to supplement, replenish, etc, a patient's hematopoietic progenitor cell population. This might be appropriate, for example, after an individual has undergone chemotherapy. There are certain genetic conditions wherein hematopoietic progenitor cell numbers are decreased, and the methods of the invention may be used in these situations as well.

It also is possible to take the increased numbers of hematopoietic progenitor cells produced according to the invention and stimulate them with hematopoietic growth agents that promote hematopoietic cell maintenance, expansion and/or differentiation, to yield the more mature blood cells, in vitro. Such expanded populations of blood cells may be applied in vivo as described above, or may be used experimentally as will be recognized by those of ordinary skill in the art. Such differentiated cells include those described above, as well as T cells, plasma cells, erythrocytes, megakaryocytes, basophils, polymorphonuclear leukocytes, monocytes, macrophages, eosinohils and platelets.

In the preferred embodiments of the invention, the hematopoietic progenitor cells are continuously cultured for an extended period of time, and aliquots of the cultured cells are harvested spaced apart in time or intermittently. "Harvesting hematopoietic cells" is defined as the dislodging or separation of cells from the matrix. This can be accomplished using a number of methods, such as enzymatic, centrifugal, electrical or by size, or the one preferred in the present invention, by flushing of the cells using the media in which the cells are incubated. The cells can be further collected and separated. "Harvesting steps spaced apart in time" or "intermittent harvest of cells" is meant to indicate that a portion of the cells are harvested, leaving behind another portion of cells for their continuous culture in the established media, maintaining a continuous source of the original cells and their characteristics. Harvesting "at least a portion of" means harvesting a subpopulation of or the entirety of. Thus, as will be understood by one of ordinary skill in the art, the invention can be used to expand the number of hematopoietic progenitor cells, all the while harvesting portions of those cells being expanded for treatment to develop even larger populations of differentiated cells.

In all of the culturing methods according to the invention, except as otherwise provided, the liquid cell culture media 15 utilized herein are conventional media for culturing cells. Examples include RPMI, DMEM, ISCOVES, etc. Typically these media are supplemented with human or animal plasma or serum. Such plasma or serum can contain small amounts of hematopoietic growth factors. The media used according to the present invention, however, can depart, in certain embodiments, from that used conventionally in the prior art. In particular, hematopoietic progenitor cells can be cultured on the matrices and devices described above for extended periods of time without the need for adding any exogenous growth agents (other than those which may be contained in plasma or serum, hereinafter "serum"), without inoculating the environment of the culture with stromal cells and without using stromal cell conditioned media.

In a continuous cell culture system, it is preferred to add and remove the cell culture media 15 from the vessel 10 at a rate of less than ½ volume change per day.

The growth agents of particular interest in connection with the present invention are hematopoietic growth factors. By hematopoietic growth factors, it is meant factors that influence the survival, proliferation or differentiation of hematopoietic cells. Growth agents that affect only survival and proliferation, but are not believed to promote differentiation, include the interleukins 3, 6 and 11, stem cell ligand and FLT-3 ligand. Hematopoietic growth factors that promote differentiation include the colony stimulating factors such as GMCSF, GCSF, MCSF, Tpo, Epo, Oncostatin M, and interleukins other than IL-3, 6 and 11. The foregoing factors are well known to those of ordinary skill in the art.

Most are commercially available. They can be obtained by purification, by recombinant to methodologies or can be derived or synthesized synthetically.

In one embodiment of the invention, the hematopoietic progenitor cells are cultured in an environment that is free of inoculated stromal cells, stromal cell conditioned medium and exogenously added hematopoietic growth factors that promote differentiation of hematopoietic cells, other than serum. By "inoculated" stromal cells, it is meant that the cell culture chamber is free of stromal cells which have been introduced into the chamber as an inoculum for promoting survival, proliferation or differentiation of the hematopoietic progenitor cells, excluding, however, stromal cells which are contained naturally in the isolate blood product.

"Stromal cells" as used herein comprise fibroblasts and mesenchymal cells, with or without other cells and elements, and can be seeded prior to, or substantially at the same time as the hematopoietic progenitor cells, therefore establishing conditions that favor the subsequent attachment and growth of hematopoietic progenitor cells. Fibroblasts can be obtained via a biopsy from any tissue or organ, and include fetal fibroblasts. These fibroblasts and mesenchymal cells may be transfected with exogenous DNA that encodes, for example, one of the hematopoietic growth factors described above.

"Stromal cell conditioned medium" refers to medium in which the aforementioned stromal cells have been incubated. The incubation is performed for a period sufficient to allow the stromal cells to secrete factors into the medium. Such "stromal cell conditioned medium" can then be used to supplement the culture of hematopoietic progenitor cells promoting their proliferation and/or differentiation.

Thus, when cells are cultured without any of the foregoing agents, it is meant herein that the cells are cultured without the addition of such agent except as may be present in serum, ordinary nutritive media or within the blood product isolate, unfractionated or fractionated, which contains the hematopoietic progenitor cells.

The culture of the hematopoietic cells (and/or of any other cell type for that matter) preferably occurs under conditions to increase the number of such cells and/or the colony forming potential of such cells. The conditions used refer to a combination of conditions known in the art (e.g., temperature, $CO_2$ and $O_2$ content, nutritive media, etc.). The time sufficient to increase the number of cells is a time that can be easily determined by a person skilled in the art, and can vary depending upon the original number of cells seeded. As an example, discoloration of the media can be used as an indicator of confluency. Additionally, and more precisely, different volumes of the blood product can be cultured under identical conditions, and cells can be harvested and counted over regular time intervals, thus generating the "control curves". These "control curves" can be used to estimate cell numbers in subsequent occasions.

The conditions for determining colony forming potential are similarly determined. Colony forming potential is the ability of a cell to form progeny. Assays for this are well known to those of ordinary skill in the art and include seeding cells into a semi-solid, treating them with growth factors and counting the number of colonies.

In certain embodiments, when hematopoietic progenitor cells are cultured in any of the foregoing devices and according to any of the foregoing methods of the invention in an environment that promotes hematopoietic progenitor cell differentiation, differentiated cells of non-hematopoietic lineage can also be produced.

In some embodiments, the environment comprises factors that direct differentiation of hematopoietic progenitor cells to produce differentiated cells of non-hematopoietic lineage selected from the group consisting of mesenchymal, parenchymal, neuronal, endothelial, and epithelial cells. In a certain embodiment, the hematopoietic progenitor cells are $CD34^-$ cells, and the environment comprises growth factors selected from the group consisting of bFGF and TGF-β, to produce mesenchymal cells. In a further embodiment, the hematopoietic progenitor cells are $CD34^+$ and/or $CD34^-$ cells, and the environment comprises growth factors selected from the group consisting of putrescine, progesterone, sodium selenite, insulin, transferrin, EGF, NGF, and bFGF, to produce neuronal cels. In a yet further embodiment, the hematopoietic progenitor cells are $CD34^+$ and/or $CD34^-$, and the environment comprises growth factors selected from the group consisting of IL-3, SCF, TGF-β1, and Flk-2/Flt-3 ligand, to produce epithelial cells. In a yet further embodiment, the hematopoietic progenitor cells are $CD34^+$ and/or $CD34^-$, and the environment comprises VEGF, to produce endothelial cells. In a still further embodiment the hematopoietic progenitor cells are $CD34^+$ and/or $CD34^-$ and the environment comprises EGF, bFGF, and SF/HGF, to produce parenchymal cells.

The invention embraces devices and methods of culturing cells in such devices that comprise a three-dimensional porous matrix member. Such matrix member as defined herein, refers to a porous, solid matrix, which is a three-dimensional structure with "sponge-like" continuous pores forming an interconnecting network. The matrix can be rigid or elastic, and it provides a scaffold upon which cells can grow throughout. Its pores are interconnected and provide the continuous network of channels extending through the matrix and also permit the flow of nutrients throughout. A preferred matrix is an open cell foam matrix having a percent open space of at least 50% and preferably 75%. Thus, it is preferred that the open space comprise the majority of the matrix. This is believed to maximize cell migration, cell—cell contact, space for cell growth and accessibility to nutrients. It is preferred that the porous matrix be formed of a reticulated matrix of ligaments which at their center point are less than 150 μm in diameter, preferably 60%, whereby a cell can reside on or interact with a portion of the ligament. Preferably, the average pore diameter is on the order of 300 μm, which resembles cancellous bone. Suitable matrices can be obtained using a number of different methods. Examples of such methods include solvent casting or extraction of polymers, track etching of a variety of materials, foaming of a polymer, the replamineform process for hydroxyapatite, and other methodologies well known to those of ordinary skill in the art. The materials employed can be natural or synthetic, including biological materials such as proteins, hyaluronic acids, synthetic polymers such as polyvinyl pyrolidones, polymethylmethacrylate, methyl cellulose, polystyrene, polypropylene, polyurethane, ceramics such as tricalcium phosphate, calcium aluminate, calcium hydroxyapatite and ceramic-reinforced or coated polymers. If the starting material for the scaffold is not metal, a metal coating can be applied to the three-dimensional matrix. Metal coatings provide further structural support and/or cell growth and adhesive properties to the matrix. Preferred metals used as coatings comprise tantalum, titanium, platinum and metals in the same element group as platinum, niobium, hafnium, tungsten, and combinations of alloys thereof. Coating methods for metals include a process such as CVD (Chemical Vapor Deposition).

The preferred matrix, refered to herein throughout as Cellfoam (Cytomatrix, Woburn, Mass.), is described in detail in U.S. Pat. No. 5,282,861, and is incorporated herein by reference. More specifically, the preferred matrix is a reticulated open cell substrate formed by a lightweight, substantially rigid foam of carbon-containing material having open spaces defined by an interconnecting network, wherein said foam material has interconnected continuous channels, and a thin film of metallic material deposited onto the reticulated open cell substrate and covering substantially all of the interconnecting network to form a composite porous biocompatible material creating a porous microstructure similar to that of natural cancellous bone.

Additionally, such matrices can be coated with biological agents which can promote cell adhesion for the cultured hematopoietic progenitor cells, allowing for improved migration, growth and proliferation. Moreover, when these matrices are used for the in vivo maintenance, expansion and/or differentiation of hematopoietic progenitor cells (i.e., when the matrices with the cells are implanted into a subject, —see also discussion below), biological agents that promote angiogenesis (vascularization) and biological agents that prevent/reduce inflammation may also be used for coating of the matrices. Preferred biological agents comprise collagens, fibronectins, laminins, integrins, angiogenic factors, anti-inflammatory factors, glycosaminoglycans, vitrogen, antibodies and fragments thereof, functional equivalents of these agents, and combinations thereof.

Angiogenic factors include platelet derived growth factor (PDGF), vascular endothelial growth factor (VEGF), basic fibroblast growth factor (bFGF), bFGF-2, leptins, plasminogen activators (tPA, uPA), angiopoietins, lipoprotein A, transforming growth factor-β, bradykinin, angiogenic oligosaccharides (e.g., hyaluronan, heparan sulphate), thrombospondin, hepatocyte growth factor (also known as scatter factor) and members of the CXC chemokine receptor family. Anti-inflammatory factors comprise steroidal and nonsteroidal compounds and examples include: Alclofenac; Alclometasone Dipropionate; Algestone Acetonide: Alpha Amylase; Amcinafal; Amcinafide; Amfenac Sodium; Amiprilose Hydrochloride; Anakinra; Anirolac; Anitrazafen; Apazone; Balsalazide Disodium; Bendazac; Benoxaprofen; Benzydamine Hydrochloride; Bromelains; Broperamole; Budesonide; Carprofen; Cicloprofen; Cintazone; Cliprofen; Clobetasol Propionate; Clobetasone Butyrate; Clopirac; Cloticasone Propionate; Cormethasone Acetate; Cortodoxone; Deflazacort; Desonide; Desoximetasone; Dexarnethasone Dipropionate; Diclofenac Potassium; Diclofenac Sodium; Diflorasone Diacetate; Diflumidone Sodium; Diflunisal; Difluprednate; Diftalone; Dimethyl Sulfoxide; Drocinonide; Endrysone; Enlimomab; Enolicarn Sodium; Epirizole; Etodolac; Etofenamate; Felbinac; Fenamole; Fenbufen; Fenclofenac; Fenclorac; Fendosal; Fenpipalone; Fentiazac; Flazalone; Fluazacort; Flufenamic Acid: Flumizole; Flunisolide Acetate; Flunixin; Flunixin Meglumine; Fluocortin Butyl; Fluorometholone Acetate; Fluquazone; Flurbiprofen; Fluretofen; Fluticasone Propionate; Furaprofen; Furobufen; Halcinonide; Halobetasol Propionate; Halopredone Acetate; Ibufenac; Ibuprofen; Ibuprofen Aluminum; Ibuprofen Piconol; llonidap; Indomethacin; Indomethacin Sodium; Indoprofen; Indoxole: Intrazole; Isoflupredone Acetate; Isoxepac; Isoxicarn; Ketoprofen; Lofemizole Hydrochloride: Lornoxicarn; Loteprednol Etabonate; Meclofenamate Sodium; Meclofenamic Acid; Meclorisone Dibutyrate; Mefenamic Acid; Mesalamine; Meseclazone; Methylprednisolone Suleptanate; Momiflumate; Nabumetone; Naproxen; Naproxen Sodium; Naproxol; Nimazone; Olsalazine Sodium; Orgotein; Orpanoxin; Oxaprozin: Oxyphenbutazone: Paranyline Hydrochloride; Pentosan Polysulfate Sodium; Phenbutazone Sodium Glycerate; Pirfenidone; Piroxicam; Piroxicam Cinnarnate; Piroxicarn Olamine; Pirprofen; Prednazate; Prifelone; Prodolic Acid; Proquazone; Proxazole; Proxazole Citrate; Rimexolone; Romazarit; Salcolex; Salnacedin; Salsalate; Sanguinarium Chloride; Seclazone; Sermetacin; Sudoxicam; Sulindac; Suprofen; Talmetacin; Talniflumate; Talosalate; Tebufelone; Tenidap; Tenidap Sodium, Tenoxicam; Tesicam; Tesimide; Tetrydamine; Tiopinac; Tixocortol Pivalate; Tolmetin; Tolmetin Sodium; Triclonide; Triflumidate; Zidometacin; Zomepirac Sodium.

The invention will be more fully understood by reference to the following examples. These examples, however, are merely intended to illustrate the embodiments of the invention and are not to be construed to limit the scope of the invention.

EXAMPLES

In all of the culturing methods according to the invention, except as otherwise provided, the liquid cell culture media 15 utilized herein are conventional media for culturing cells. Examples include RPMI, DMEM, ISCOVES, etc. Typically these media are supplemented with human or animal plasma or serum. In a continuous culture system, it is preferred to add and remove the media from the vessel 10 at a rate of less than ½ volume change per day.

Preferably the cells being cultured on the three-dimensional matrix members used in various embodiments of the invention are animal cells, plant cells, eukaryotic cells, prokaryotic cells, mammalian cells, or genetically engineered cells. The cells being grown may be from one or more cell lines, and the cells being grown may be tissues or components of tissues. Also, the cells being grown may be multi-cell assemblies.

The matrix material used in each embodiment of the invention, when culturing cells, may be precoated with a biological agent such as collagen, fibronectin, laminin, integrin, angiogenic factor, anti-inflammatory factor, glycosaminoglycan, vitrogen, and antibody, or fragments thereof, or combinations thereof.

With respect to apparatus 5, the drive member 42 (e.g., stirring assembly) is initiated to cause the three dimensional porous matrix material to move through the nutrient growth medium, and cells are grown on the matrix material during such motion.

To test the effectiveness of the "spinner flask" rotational cell culture system of the invention to support in vitro cell growth, apparatus 5 was used for culturing mammalian cells and the results of the culturing were compared with a control. The cell types used in these experiments were 5/9 alpha CHO (Chinese hamster ovary) cells. 5/9 alpha CHO cells were maintained in Minimum Essential alpha Medium with GlutaMax (Bibco-BRL) supplemented with 5% Fetal Bovine Serum (FBS: Sigma), 0.2 $\mu$M methotrexate, 50 units/ml penicillin, 50 $\mu$g streptomycin., and 1×Fungizone.

Prior to placing the three-dimensional porous matrix members 50 into the vessel 10 for culturing, adherent cultures were established by first seeding cells into each of the three-dimensional porous matrix members 50, as accommodated in matrix cartridge 160. Prior to seeding, the matrix members 50 (80-ppi pore density) were pre-wet with PBS. After removal of excess PBS cells, 4×10$^6$ cells in 200 $\mu$l were seeded into each matrix member 50 and allowed to adhere for 3 to 4 hours. At this time medium was added to the matrix cartridge 160 until media covered the entire unit. The cells were allowed to further adhere to each matrix member 50, overnight at 37 degrees C.; 5% $CO_2$. The following day the assembled holder 70, closure-cap 100, and matrix members 50, were removed from the matrix cartridge 160, and were placed onto support-wheel 130, shaft 30, and placed into culture in a 500 ml vessel 10. The vessel 10 was then placed on top of a magnetic stirrer 60 in a 5% $CO_2$ incubator and the matrix assembly 40 was allowed to rotate continuously at 2 rpm. Samples were taken each morning for analysis by ELISA. Cell culture media were replaced as needed (indicated by a color change in medium), and cell culture was allowed to continue on. At the end of the culture period, cells contained within each matrix member 50 were stained with crystal violet, or in some instances lysed to calculate cell number via DNA content.

To stain cells in matrix members 50 with crystal violet, each matrix member 50 was first washed in excess PBS 2x. Cells were fixed to matrix member 50 by incubation in 1% glutaraldehyde in PBS for 10 minutes at room temperature with occasional mixing. The glutaraldehyde solution was aspirated and the matrix members 50 were washed again 2xin excess PBS. Units were then incubated in 0.5% crystal violet/PBS solution for 10 minutes at room temperature with occasional mixing. The matrix members 50 were each extensively rinsed in deionized water until each unit rinsed clear. Excess fluid was removed from the unit and they were allowed to dry overnight.

Figure 8:
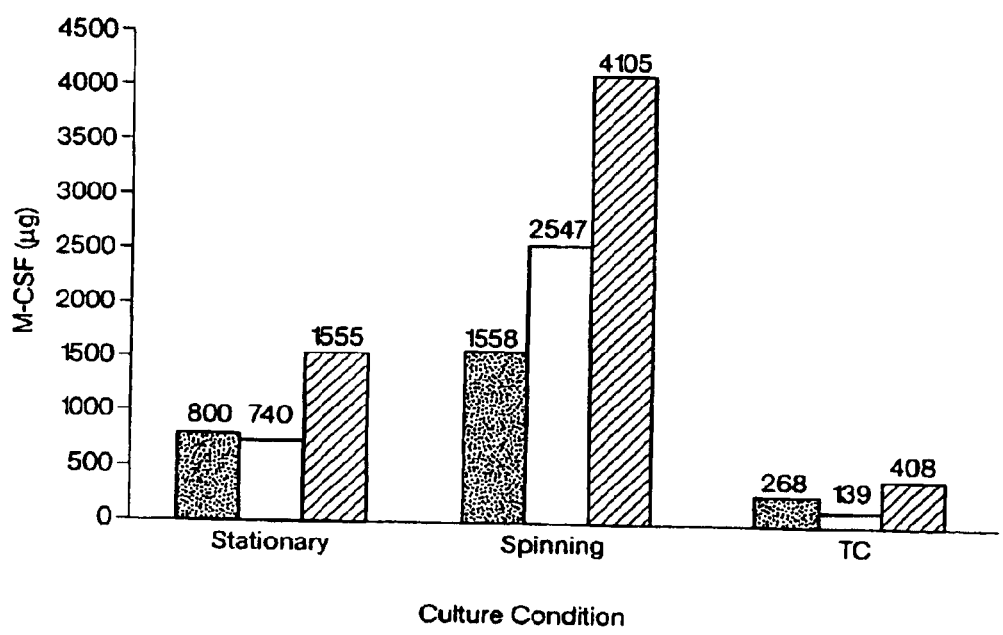
FIG. 8 shows a graph of test results relating to cumulative M-CSF production under stationary and spinning culture conditions.

Following culture, the extent to which 5/9 alpha cells grew on matrix members 50 in vessel 10, with and without rotation, was compared to cells grown on matrix members 50 in tissue culture plates as a control. As can be seen in FIG. 8, the pattern of crystal violet staining indicates that 5/9 alpha cells seeded onto matrix members 50 grew to a greater density and with more complete coverage of the matrix member 50 when grown in the vessel 10 as compared to when grown in the control tissue culture dish (flat dish). Cell coverage was also substantially greater in the matrix member 50 from vessel 10 with rotation as compared to a matrix member 50 from vessel 10 without rotation (FIG. 8).

5/9 alpha cells are stably transfected with the gene encoding human megakaryocyte colony stimulating factor (M-CSF), which is constitutively secreted, and can be quantified using ELISA analysis. To assess the production of M-CSF from cultured 5/9 alpha cells, media samples taken daily from each culture condition were analyzed for the amount of M-CSF present by ELISA. M-CSF production was sustained throughout the time course of this experiment (19 days) in all culture conditions. M-CSF production, depicted as concentration, in the control tissue culture dish containing a matrix member 50 was 4.9 µg/ml, compared to 4.5 µg/ml in the matrix members 50 from vessel 10 with rotation, and 1.3 µg/ml in the matrix member 50 from vessel 1 without rotation. However, when the total production of M-CSF was examined, the rotating matrix member 50 had a much higher level of total M-CSF after 19 days of culture as compared to the matrix member 50 in the plate. Additionally, the rotating matrix member 50 also had a significantly higher total production of M-CSF as compared to the stationary matrix member 50. 4105 µg vs. 1555 µg. Together these data indicate that using a three-dimensional porous material such as Cellfoam in matrix member 50 in the spinner flask leads to a greater total production of M-CSF as compared to conventional static culturing methods. The ability to rotate or "spin" each matrix member 50, greatly increases the effectiveness of using Cellfoam material in the spinner flask culturing vessel 10, increasing the total yield of M-CSF, in this case 2.6 flood in the current experiment. The production from the rotating spinner flask was 10 fold greater than conventional static culture of Cellfoam in a control tissue culture dish.

To examine the modularity and flexibility of the spinner flask of the invention, apparatus 5 was tested using matrix members 50 that allowed for variations in the number and size of the matrix members that could be used in the spinner flask. The Cellfoam matrix member 50 were held in position by matrix assembly 40 including shaft 30, in the vertical position as depicted in FIG. 1. Difference in culture performance was first examined when apparatus 5 was seeded with either 12 or 36 matrix members 50. The Cellfoam matrix members 50 used in this experiment were 15x15 mm squares, 5 mm in thickness, having a porosity of 65 ppi. The fact that these Cellfoam matrix members were 65 ppi allowed us to also test whether this decrease in pore density had any affect on the ability of the 5/9 alpha cells to grow in the spinner vessel.

Cellfoam matrix members 50 were prepared as above and were each seeded with $2 \times 10^6$ 5/9 alpha cells in a volume of 100 µl. After overnight incubation to allow cells to adhere in matrix cartridges 160, matrix assemblies 40 (holder 70 and closure-cap 100), were attached onto a support-wheel 130. Analysis of a subset of matrix members 50 indicated that $3/10^5$ cells remained attached to each matrix member 50 before being placed on holders 70 for assembly on the support-wheel 130. Once assembled, the matrix assembly 40 was placed into a spinner vessel 10 with approximately 500 ml of media. Two spinner vessels flasks were set up, one with 3 holders 70 (12 matrix members 50), and a second with 9 holders 70 (12 matrix members 50). The assemblies were continuously rotated at a speed of approximately 2 rpm for 190 hr (8 days). They were compared to a control tissue culture dish, without Cellfoam matrix material (i.e., flat, 2-Dimensional culture), that had $1.5 \times 10^6$ cells seeded the same day as cells were seeded onto the matrix members 50.

Crystal violet staining was performed on matrix members 50 at the end of the experiment to determine cell distribution throughout the individual matrix members 50 of each assembly. This analysis indicated that the 5/9 alpha cells were able to grow throughout each matrix member 50 of the assembly. Next, matrix assemblies were screened for cellular metabolism analytes by a NOVA biomedical Bioprofile 200. This instrument allowed for the determination of up to 12 different analytes within the supernatant media at multiple time points throughout the culture period. Four analytes were of particular interest to these assembly experiments, glucose, pH, lactate and $pO_2$. Glucose consumption was most rapid in the control (flat) tissue culture dish over the first 48 hours of the experiment whereupon it completely depleted the media of glucose. The 9 matrix assemblies had a slightly lower rate of glucose consumption as compared to the control, but it too eventually depleted the media glucose. The 3 matrix assemblies had the slowest rate of glucose consumption, depleting the media down to 0.25 g/ml by 96 hours. This is probably reflective of the fact that the plate had the highest initial cell to medium volume ratio (50,000 cells/ml) at the start of the experiment, compared to the 9 matrix assemblies, which had an estimated 14,000 cells/m, and the 3 matrix assemblies which had an estimated 5,000 cells/ml at startup. Since 2 out of 3 conditions were completely depleted of glucose, media for all conditions was replaced with fresh media.

At this point all 3 culture conditions depleted their source of glucose over the next 48 hours with identical kinetics. Media was refreshed in the matrix assembly cultures at 144 hours and their glucose consumption was again rapid with the 9 matrix assemblies showing the most rapid depletion of glucose, suggesting that this culture has a greater metabolic potential at this later time than the 3 matrix assembly spinner flask.

We next looked at the consumption of the dissolved oxygen. The consumption of dissolved oxygen was greatest in the 9 matrix assembly with the 3 matrix assembly lagging slightly behind. Unlike the scenario with glucose consumption, the control did not consume oxygen at either the same rate or to the same extent as the 3 and 9 matrix assembly spinner flasks. After the change of media at 96 hours for all culture conditions the depletion of dissolved oxygen was very rapid in both assembly spinner flasks, eventually getting down to the same level after 48 additional hours as was achieved during the first 96 hours of culture, indicating a very highly metabolically active culture. Interestingly, 24 hours after the change of media (at 144 hours) the dissolved oxygen was down to the same level as before the media change indicating high levels of metabolic activity.

The production of lactate mirrored the consumption of glucose and oxygen. Lactate production was most rapid in the plate in the first 48 hours, eventually reaching a plateau at just under 1 g/l. By 96 hours, the 12 skewer assembly had the highest level of lactate present, a level higher than the plate, with the 4 skewer spinner lagging behind both. The change of media at 96 hours eliminated the lactate from the cultures at which time all 3 cultures begin to generate lactate with equal kinetics in the freshened media. All 3 cultures reached the same maximum after an additional 48 hours at which time the second media change is made within the 3 and 9 matrix assembly vessels only. As was the case with the glucose and oxygen profiles, lactate productions was most rapid in the 9 matrix assembly, again indicating a greater metablolic potential.

Finally, the pH profile of these cultures was examined. As was the case for glucose, pH declined most rapidly over the first 48 hours of the experiment in the control, although the 9 matrix assembly was not markedly behind. Again the 3 matrix assembly showed the slowest build up of pH, not unexpected based on the glucose profile. Interestingly, although over the next 48 hours of the experiment the pH for the 3 and 9 matrix assembly declined, the pH in the plate seemed to level off around 7.1. The reason for this is unclear, though it may have to do with a switch in metabolism from glucose to lactate in this culture. As noted before, the media was changed at 96 hours and therefore the pH was restored to is initial level. The pH over the next 24–48 hours declined extremely rapidly in the 3 and 9 matrix assembly vessels, eventually lying outside the measurable range for the instrument, which at the low end is pH 6.

The production of M-CSF in these cultures was also measured. Over the first 96 hours of the experiment the amount of M-CSF produced in each culture increased. Although the control had the highest concentration of M-CSF produced, the total M-CSF produced was mush greater in the 3 and 9 matrix assemblies. Over the first 96 hours total M-CSF production for the 9 matrix assembly was 1597.5 µg, 1320 µg for the 3 matrix assembly, and 115.6 µg for the control. Over the next 96 hours of the experiment M-CSF production in the control plate was similar to control plate in the previous experiment. However, the 3 and 9 matrix assemblies did not produce M-CSF to a level expected from production in the first 96 hours. This is probably due to the extremely low pH and oxygen levels in the present in these cultures at this time, which can cause many proteins to be degraded.

All references disclosed herein are incorporated by reference in their entirety.

We claim:

1. A matrix assembly for culturing cells, comprising:
   a holder having a pair of substantially parallel arms connected together at one end by a base arm and having an open end at the other,
   a mounting device joined to the base arm for mounting the holder to a support,
   a groove in each of the arms generally facing one another, and
   at least one three-dimensional porous matrix member having its periphery removably disposed in the groove of each arm.

2. A matrix assembly as claimed in claim 1, wherein the holder is generally U-shaped.

3. A matrix assembly, comprising:
   a holder having a pair of spaced apart coplanar arms connected together at one by a base arm and having an open end at the other,
   at least one three-dimensional porous matrix member carried by the arms and detachably connected thereto, said three-dimensional porous matrix member being disposed between and in the plane of the arms,
   a mounting device attached to the base arm for mounting the holder to a support, and
   a closure-cap detachably mounted to the open end of the arms for preventing the three-dimensional porous matrix member being withdrawn from between the arms, said closure-cap having a handle for stripping the closure-cap from the holder and for carrying the assembly without touching the three-dimensional porous matrix member.

4. A matrix assembly as claimed in claim 3, wherein the holder is generally U-shaped.

5. A support and matrix assembly for culturing cells, comprising:
   a shaft for disposition in vessel containing liquid cell structure media,
   a support-wheel mounted on the shaft and having a plurality of arms extending outwardly away from the shaft, each of said arms having at least one station for carrying a matrix assembly,
   a plurality of matrix assemblies mounted on each of the stations, each assembly including a holder having a pair of generally parallel and spaced apart arms connected together at one end by a base arm and having an open end at the other,
   a mounting device attached to the base arm for mounting the holder to the station on the arm of the support-wheel,
   a groove on each of the arms of the holder facing one another for supporting three-dimensional porous matrix members between and generally in the plane of the arms, and
   a closure-cap for each of the holders for retaining the three-dimensional porous matrix member, between the arms.

6. A support and matrix assembly as claimed in claim 5, wherein the holder is generally U-shaped.

7. A matrix cartridge for culturing cells, comprising:
   a holder having a pair of spaced apart coplanar arms connected together at one end by a base arm and having an open end at the other, at least one three-dimensional porous matrix member carried by the arms and detachably connected thereto, said three-dimensional porous matrix member being disposed between and in the plane of the arms, a mounting device attached to the base arm for mounting the holder to a support, a closure-cap detachably mounted to the open end of the arms for preventing the three-dimensional porous matrix member being withdrawn from between the arms, said closure-cap having a handle for stripping the closure-cap from the holder and for carrying the assembly without touching the three-dimensional porous matrix member, and a container having a well for an assembled holder, closure-cap and three-dimensional porous matrix member, said container having a cover for sealing the well with the holder, closure-cap and three-dimensional porous matrix member.

8. A matrix cartridge as claimed in claim 7, wherein the holder is generally U-shaped.

9. A matrix assembly for culturing cells, comprising:

a support comprising a shaft, and an outwardly extending member extending from and connected to the shaft;

at least one rigid three-dimensional porous solid matrix member carried by the support for movement therewith, wherein the porous solid matrix member is a unitary structure; and wherein the support further comprises a holder attached to the outwardly extending member, the holder having a pair of substantially parallel arms connected together at one end by a base arm and having an open end at the other.

10. A matrix assembly as claimed in claim 9, wherein the holder is generally U-shaped.

* * * * *

UNITED STATES PATENT AND TRADEMARK OFFICE
CERTIFICATE OF CORRECTION

PATENT NO. : 6,991,933 B1
DATED : January 31, 2006
INVENTOR(S) : Todd M. Upton et al.

It is certified that error appears in the above-identified patent and that said Letters Patent is hereby corrected as shown below:

<u>Column 22,</u>
Line 20, insert -- end -- after "together at one".
Line 41, delete "structure" and insert -- culture --.

Signed and Sealed this

Fourth Day of April, 2006

JON W. DUDAS
*Director of the United States Patent and Trademark Office*